United States Patent [19]

Ito et al.

[11] Patent Number: 4,840,180
[45] Date of Patent: Jun. 20, 1989

[54] ULTRASONIC DIAGNOSIS APPARATUS FOR MEASUREMENT OF SPEED OF MOVING MEDIUM IN A LIVING BODY

[75] Inventors: Yukio Ito; Yutaka Sato; Shinji Kishimoto; Satoshi Tamano, all of Kashiwa, Japan

[73] Assignee: Hitachi Medical Corp., Tokyo, Japan

[21] Appl. No.: 160,754

[22] Filed: Feb. 26, 1988

Related U.S. Application Data

[63] Continuation of Ser. No. 804,608, Dec. 4, 1985, abandoned.

[30] Foreign Application Priority Data

Dec. 4, 1984 [JP] Japan .................... 59-255919

[51] Int. Cl.$^4$ ............................................. A61B 10/00
[52] U.S. Cl. ............................ 128/661.08; 73/861.25
[58] Field of Search ................. 128/660, 661, 663; 73/861.25, 861.06

[56] References Cited

U.S. PATENT DOCUMENTS

4,573,477 3/1986 Namekawa et al. .......... 73/861.25

Primary Examiner—MaryAnn Lastova
Attorney, Agent, or Firm—Antonelli, Terry & Wands

[57] ABSTRACT

An ultrasonic diagnosis apparatus comprises an ultrasonic probe for transmitting an ultrasonic pulse beam toward an internal moving medium of a living body at a constant recurrence frequency, a converter for mixing the received high-frequency signal with a set of complex reference signals having a frequency n times as high as the recurrence frequency of the transmitted ultrasonic pulse beam and having a complex relation therebetween, thereby converting the high-frequency signal into complex signals, a speed operating circuit for computing the moving speed of the internal moving medium on the basis of the complex signals, and a display unit for displaying the moving speed in real time. The apparatus may include a speed dispersion operating circuit for computing the dispersion of the moving speed computed by the speed operating circuit in order to display both the moving speed and the dispersion thereof on the display unit.

4 Claims, 5 Drawing Sheets

ULTRASONIC DIAGNOSIS APPARATUS FOR MEASUREMENT OF SPEED OF MOVING MEDIUM IN A LIVING BODY

CROSS REFERENCE TO RELATED APPLICATION

This application is related to application Ser. No. 806,394, filed Dec. 9, 1985, which is commonly assigned.

BACKGROUND OF THE INVENTION

This invention relates to the art of measurement for detecting the state of motion of an internal moving medium of a living body, and more particularly to a novel technique which is effectively, applicable to an ultrasonic diagnosis apparatus used for measurement of the moving speed (referred to hereinafter simply as speed) of an internal moving medium of a living body or measurement of the moving speed and moving speed dispersion (referred to hereinafter simply as speed dispersion) of such a moving medium.

An ultrasonic pulse-Doppler method has been put into practical use for the measurement of the speed of an internal moving medium of a living body, for example, a visceral organ such as the heart or a fluid such as blood or humor in a circulatory organ.

A prior art, ultrasonic diagnosis apparatus utilizing the ultrasonic pulse-Doppler method described above is disclosed in, for example, Jpaanese Unexamined Patent Publication No. 58-188433 (JP-A-58-188433) laid open on Nov. 2, 1983. In the cited patent publication, an autocorrelator is employed for converting a high-frequency signal reflected from an internal moving medium of a living body into complex signals and then computing autocorrelation between the complex signals, and a speed operator is employed to compute the speed of the moving member on the basis of the computed autocorrelation. However, the necessity for incorporation of the autocorrelator has required a complicated circuit structure resulting in a bulky overall size of the ultrasonic diagnosis apparatus.

In the prior art, ultrasonic diagnosis apparatus disclosed in the cited publication, delay line cancellers are employed together with the autocorrelator for detecting the speed of the internal moving medium of the living body on the basis of the high-frequency signal received by an ultrasonic probe and including a Doppler shift frequency. Numerical formulas used for carrying out a series of signal processing on the received high-frequency signal by the delay line cancellers and autocorrelator do not include amplitude terms, and the speed of the moving medium is computed under the assumption that the amplitude of the received high-frequency signal is constant. Consider now the case of detection of the speed of blood flow, as an example. In this case, it is limitatively assumed that the second power of the amplitude (energy) of the Doppler shift signal is proportional to the number of blood cells scanned by the ultrasonic beam, and the number of blood cells scanned by the ultrasonic beam is constant regardless of the rate of blood flow.

However, the number of blood cells scanned by the ultrasonic beam is not always constant regardless of the rate of blood flow. This is because turbulence may occur in the blood flow, and there is a concentration difference between red blood cells and white blood cells. Thus, the amplitude of the Doppler shift signal is not always constant. Further, although the power of the ultrasonic signal attenuates while the ultrasonic signal is received after it is transmitted into the living body, the amount of beam attenuation varies depending on the tissue structure of the scanned portion of the living body. Therefore, in the case of a moving medium such as the heart where the momentum is large, the state of the tissue structure, through which the ultrasonic beam passes, varies continuously, and it is unable to always receive a high-frequency signal including a Doppler shift signal having a constant amplitude.

Thus, the prior art manner of signal processing, according to which the average speed is computed under the assumption the amplitude of the received signal is always constant, has been defective in that an error is inevitably included in the result of computation.

SUMMARY OF THE INVENTION

It is an object of the present invention to provide an ultrasonic diagnosis apparatus which can measure the speed of an internal moving medium of a living body using a simplified circuit structure not employing the autocorrelator incorporated in the prior art apparatus.

Another object of the present invention is to provide an ultrasonic diagnosis apparatus which can measure the speed dispersion is addition to the speed of an internal moving medium of a living body using a simplified circuit structure not requiring the autocorrelator. The measurement of the speed dispersion is made in the case where the moving member is a fluid in a living body such as blood or humor.

According to the present invention, an ultrasonic beam transmitted toward and reflected from an internal moving part of a living body is received and amplified, and, after conversion of the reflected wave into complex signals, the speed of the moving part is immediately computed by a speed operating circuit on the basis of the complex signals. In addition to the measurement of the speed of the moving member, the speed dispersion can also be computed by a speed dispersion operating circuit. Further, the speed operating circuit and the speed dispersion operating circuit are preferably those operable at a high speed so that individual points lying in the depthwise direction of the directed ultrasonic beam can be measured in real time.

DESCRIPTION OF THE PREFERRED EMBODIMENTS

A preferred embodiment of the present invention showing an application of the present invention to an ultrasonic diagnosis apparatus adapted to acquire information of an internal moving medium of a living body according to an ultrasonic pulse-Doppler method, will now be described in detail with reference to the accompanying drawings. In the drawings, the same reference numerals are used to designate the same functional parts.

Figure 1:
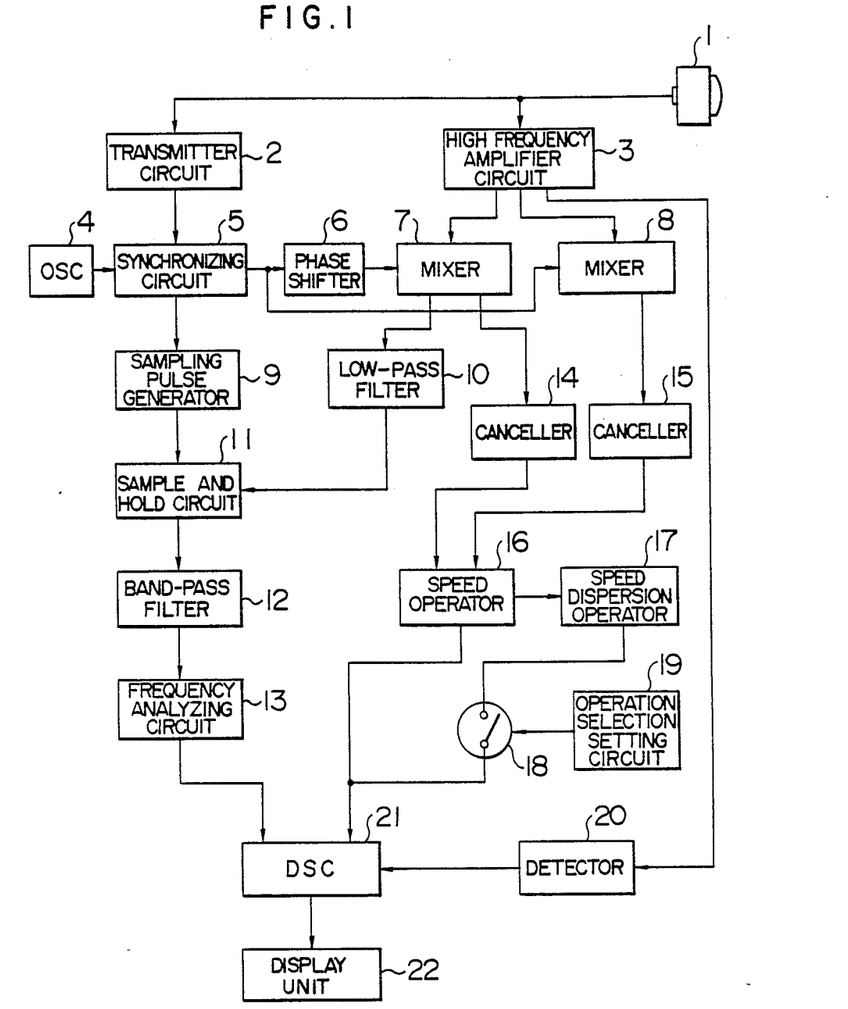
FIG. 1 is a block diagram showing the general structure of a preferred embodiment of the ultrasonic diagnosis apparatus according to the present invention.

Referring to FIG. 1, an ultrasonic beam transmitted toward an internal moving medium of a living body from an ultrasonic probe 1 is produced by a transmitter circuit 2. Pulses of the transmitted ultrasonic beam are reflected from the internal moving medium of the living body to be received by the ultrasonic probe 1. The received high-frequency signal including internal information of the living body is amplified by a high-frequency amplifier circuit 3. A crystal oscillator 4 generates a high-frequency synchronizing signal. This high-frequency synchronizing signal is converted by a synchronizing circuit 5 into a reference signal having a frequency corresponding to the recurrence frequency of the ultrasonic pulses transmitted from the ultrasonic probe 1. The phase of the reference signal generated from the synchronizing circuit 5 is shifted by 90° by a phase shifter 6. The 90°—phase shifted reference signal from the phase shifter 6 is mixed with the amplified received signal in a first mixer 7 which acts to provide information of the moving direction of the moving medium which is, for example, blood flow. On the other hand, the reference signal from the synchronizing circuit 5 is directly mixed with the amplified received signal in a second mixer 8.

A first canceller 14 and a second canceller 15 extract only Doppler components having information of the internal moving medium of the living body from the output signals of the first and second mixers 7 and 8 respectively. A speed operating circuit 16 computes the speed of the internal moving medium of the living body on the basis of the canceller output signals representing the extracted Doppler components. A speed dispersion operating circuit 17 computes the value of speed on the basis of the value of the speed computed by the speed operating circuit 16. The received signal is thus converted by the speed operating circuit 16 and speed dispersion operating circuit 17 into a signal indicative of the speed and a signal indicative of the speed deviation. An operation selector switch 18 is provided to determine whether the speed only is to be computed or whether both the speed and the speed dispersion are to be computed. This operation selector switch 18 is changed over under control of an operation selection setting circuit 19. The operation selector switch 18 may be disposed between the speed operating circuit 16 and the speed dispersion opreating circuit 17. A detector 20 detects the received signal including the internal information of the living body and amplified by the high-frequency amplifier circuit 3 so as to extract a sectional image signal of the internal moving medium of the living body. This extracted sectional image signal is written in a digital scan converter (abbreviated hereinafter as a DSC) 21.

The high-frequency component of the output signal of the first mixer 7 is removed by a low-pass filter 10, and the output signal of the low-pass filter 10 is applied to a sample and hold circuit 11. In order to extract a one-dimensional Doppler shift component from the output signal of the low-pass filter 10 in a usual manner, a gate pulse signal produced by a sampling pulse generator 9 is applied to the sample and hold circuit 11 thereby extracting the signal representing the Doppler shift of the internal moving medium of the living body. After being smoothed by a band-pass filter 12, the Doppler shift signal is applied to a frequency analyzing circuit 13 there the one-dimensional Doppler shift signal is extracted as by high-speed Fourier transformation. This one-dimensional Doppler shift signal is also written in the DSC 21.

The signals indicative of the internal information of the living body, written in the DSC 21, are converted into a video signal in the DSC 21 and read out as a television signal to be displayed on a display unit 22 such as a CRT monitor or a television monitor.

Among the internal information of the living body, the speed and speed dispersion are computed according to arithmetic formulas or expressions described later.

In order to compute the speed and speed dispersion of an internal member at a certain predetermined depth, it is necessary to detect amounts of Doppler shift occurring in a plurality of ultrasonic waves reflected from the predetermined depth. For conveniences of description, it is supposed herein that the number of received signals is two.

Figure 2:
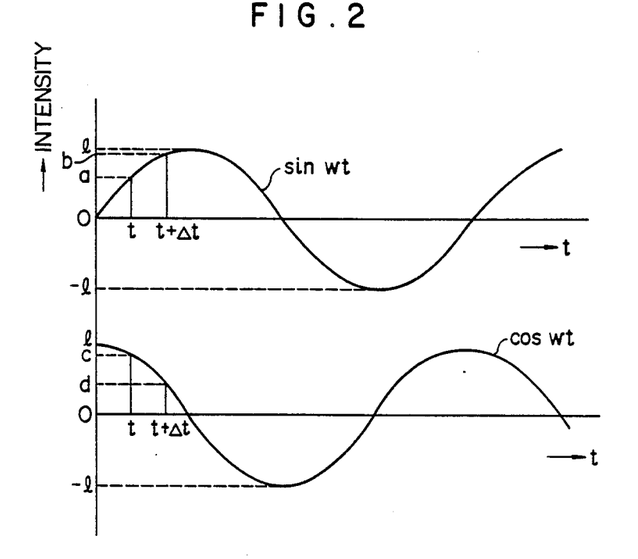
FIGS. 2 to 5 illustrate how the speed and speed dispersion are computed in the embodiment of the present invention.

The ultrasonic beam is transmitted from the ultrasonic probe 1 toward an internal moving medium of a living body at a time interval of Δt, and ultrasonic waves reflected from the internal moving 66 medium of the living body are received by the ultrasonic probe 1. When a time-dependent change of each reflection point is taken into consideration, the intensity at the reflection point of the Doppler signal extracted from each of the received signals is represented by the value, at a certain time, of a periodic function representing a certain intensity and having a period of Doppler shift. In order to detect the intensity represented by the periodic function and resulting from the Doppler shift (that is, the kinetic momentum of the internal moving medium of the living body), the combination of the phase shifter 6 and the mixers 7, 8 produces signals having a phase difference of 90° on the basis of the received signals. The intensities a, b, c and d of Doppler shift, at a certain depth, of the four signals in total are given by phases at time t and (t+Δt) as shown in FIG. 2.

More precisely, the intensities a and c, at time t, of the functions having the period (frequency) $f_d$ of Doppler shift and having the phase difference of 90° therebetween are expressed respectively as follows:

$$a = 1 \sin 2\pi f_d t \quad (1)$$

$$c = 1 \cos 2\pi f_d t \quad (2)$$

where 1 is the absolute value of the intensity of the signal received at time t.

Similarly, the intensities b and d at time (t+Δt) are expressed respectively as follows:

$$b = 1 \sin 2\pi f_d (t - \Delta t) \quad (3)$$

$$d = 1 \cos 2\pi f_d (t - \Delta t) \quad (4)$$

On the basis of these expressions (1) to (4), the absolute intensities $l_t$ and $l_{(t+\Delta t)}$ of the functions at times t and (t+Δt) are expressed respectively as follows:

$$l_t = (a^2 + c^2)^{\frac{1}{2}} \quad (5)$$

$$l_{(t+\Delta t)} = (b^2 + d^2)^{\frac{1}{2}} \quad (6)$$

These absolute intensities $l_t$ and $l_{(t+\Delta t)}$ are proportional to the flow rate of a fluid, for example, blood in the living body.

How to compute the moving speed of the fluid in the living body will next be described.

Figure 3:
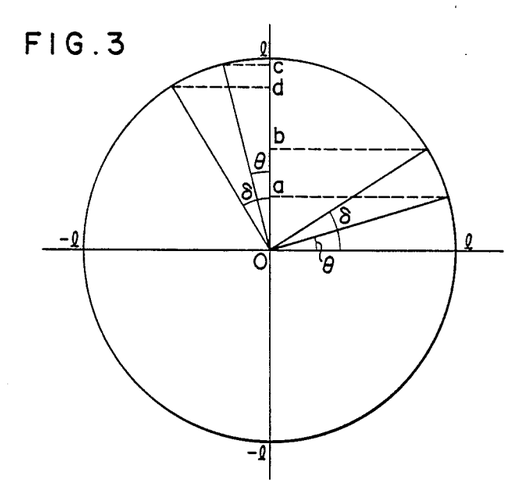

FIG. 3 illustrates that, at times t and (t +Δt), the Doppler waves have respective angular displacements θ and δ which are expressed as follows:

$$\theta = \sin^{-1}\left(\frac{a}{l_t}\right) \quad (7)$$

$$\delta = \sin^{-1}\left(\frac{b}{l_{(t+\Delta t)}}\right) \quad (8)$$

Figure 4:
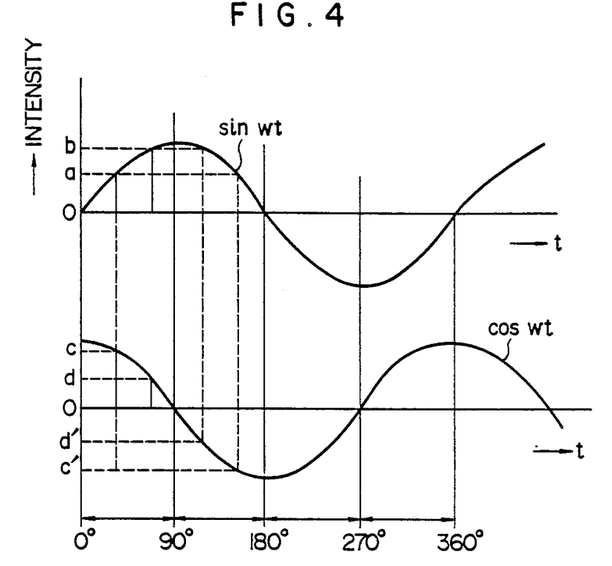
Figure 5:
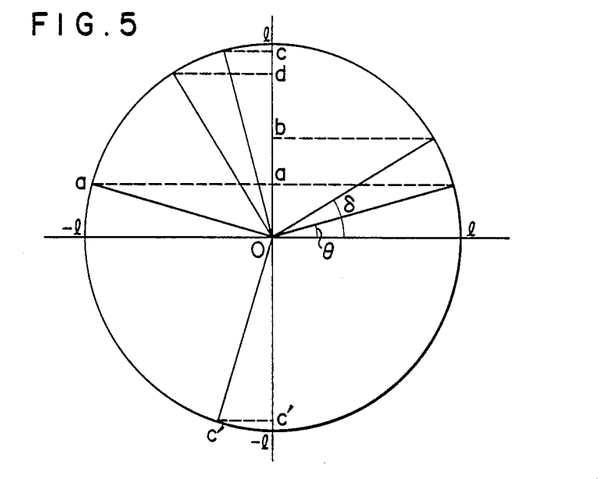

It is to be noted that the values of θ and δ determined by the expressions (7) and (8) lie within the ranges of $-90° < \theta < 90°$ and $-90° < \delta < 90°$ respectively. Therefore, in order to determine the values of θ and δ so that they lie within the ranges of $$0° < \theta < 360°, 0° < \delta < 360° \quad (9),$$

the value of θ is computed on the basis of a $(=1 \sin 2\pi f_d t)$, c $(=1 \cos 2\pi f_d t)$ and c' $[=1 \cos (\pi - 2\pi f_d t)]$, as shown in FIGS. 4 and 5. Similarly, the value of δ is computed on the basis of b $[=l \sin 2\pi f_d(t-\Delta t)]$ and d $[=1 \cos 2\pi f_d(t-\Delta t)]$.

That is, depending on whether the sine and cosine components of the signals having the phase difference of 90° are positive or negative, the value of x is $\sin^{-1} x$ lies is various ranges as shown in the following Table I:

TABLE 1

| sin component | cos component | Range of x |
|---|---|---|
| Positive | Positive | 0° < x < 90° |
| Positive | Negative | 90° < x < 180° |
| Negative | Negative | 180° < x < 270° |
| Negative | Positive | 270° < x < 360° |

On the basis of Table I, the values of θ and δ given by the expressions (7) and (8) respectively are computed. The displacement angle Δθ of θ in the minute length of time of change Δt is computed according to the following expression (10) on the basis of the expressions (7) and (8):

$$\Delta\theta = \theta - \delta \quad (10)$$

The angular velocity ω is expressed as follows:

$$\omega = \Delta\theta/\Delta t = (\delta - \theta)/\Delta t \quad (11)$$

From the above expression (11), the frequency $f_d$ of the Doppler shift is expressed as follows:

$$f_d = 2\pi \cdot \omega = 2\pi \cdot (\delta - \theta)/\Delta t$$

Since this Doppler shift frequency $f_d$ is proportional to the speed of the fluid flow in the living body, the moving direction of the fluid and the speed of the fluid flow in the living body can be computed on the basis of the Doppler shift frequency $f_d$.

The speed 16 shown in FIG. 1 computes the speed of the fluid flow in the living body according to the speed-computing expressions described above. The detailed structure of one form of the speed operating circuit 16 is shown in FIG. 6.

Figure 6:
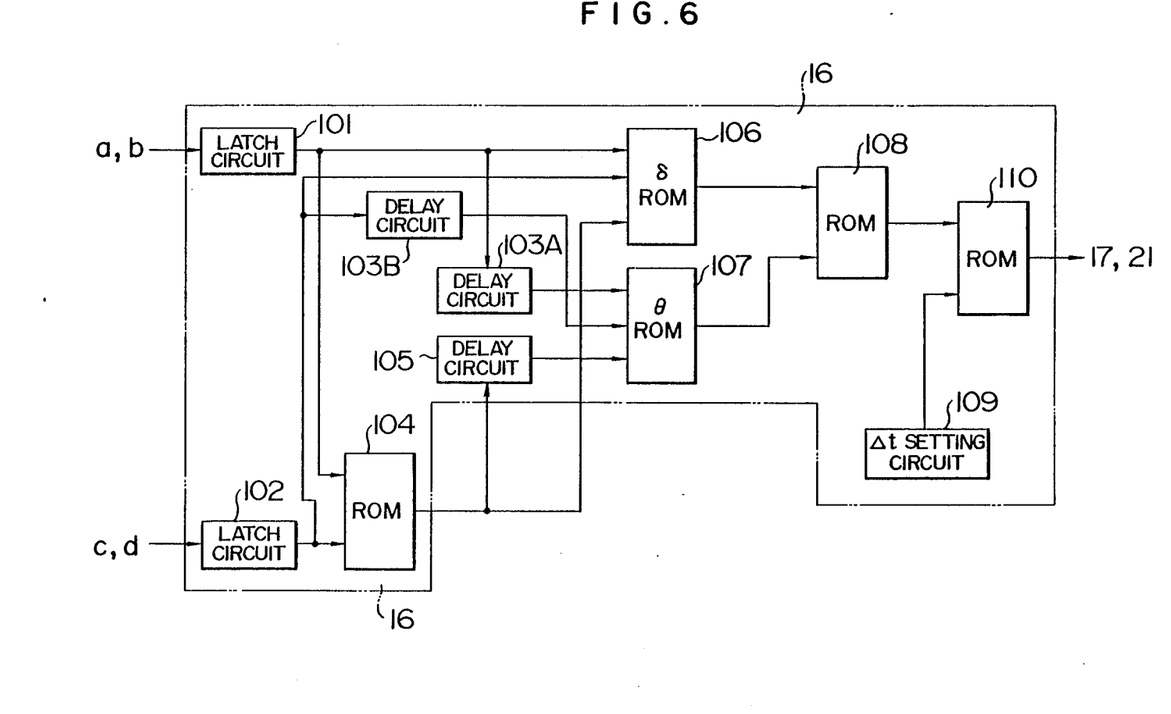
FIG. 6 is a block diagram showing the detailed structure of one form of the speed operating circuit shown in FIG. 1.

Referring to FIG. 6, the values of the sine component, [a given by the expression (1) and b given by the expression (3)], of the signals received at times t and (t+Δt) are sequentially supplied to and temporarily latched in that order in a first latch circuit 101. Similarly, the values of the cosine component, [c given by the expression (2) and d given by the expression (4)], of the signals received at the times t and (t+Δt) are sequentially supplied to and temporarily latched in that order in a second latch circuit 102.

A first delay circuit 103A is connected to the output of the first latch circuit 101 to provide the value of the sine component of the signal extracted from the preceding ultrasonic beam received from the same depth, this is, the value of a given by the expression (1). A second delay circuit 103B is connected to the output of the second latch circuit 102 to provide the value of the cosine component of the signal extracted from the preceding ultrasonic beam received from the same depth, that is, the value used for computation of $\sin^{-1}$ shown in Table I. An operator 104, which is in the form of a ROM (a read-only memory), has a table for computing the absolute value, [the value of $l_t$ given by the expression (5)], of the intensity of the received signal on the basis of the value of the sine component [a given by the expression (1)] and the value of the cosine component [c given by the expression (2)]. A third delay circuit 105 is connected to the output of the ROM 104 to provide the absolute value, [the value of $l_{(t+\Delta t)}$ given by the expression (6)], of the intensity of the signal extracted from the preceding ultrasonic beam received from the same depth. A second ROM 106 has a table for computing the value of the angle δ according to the expression (8) and Table I on the basis of the data outputs of the latch circuits 101, 102 and ROM 104. A third ROM 107 has a table for computing the value of the angle θ according to the expression (7) and Table I on the basis of the data outputs of the delay circuits 103A, 103B and 105. A fourth ROM 108 has a table for computing the value of the displacement angle Δθ according to the expression (10) on the basis of the data outputs of the ROM's 106 and 107.

A Δt setting circuit 109 sets the time internal Δt of the transmission of the ultrasonic beam from the ultrasonic probe 1. A fifth ROM 110 has a table for computing the value of the angular velocity ω given by the expression (11) on the basis of the data output of the ROM 108 and the value of the setting of the time interval Δt of ultrasonic beam transmission.

The operation of the speed operating circuit 16 having such a construction will be described with reference to FIG. 6.

The data b of the sine component of the signal extracted from the reflected wave received at time (t+Δt) is supplied from the canceller 14 shown in FIG. 1 to the first latch circuit 101, and the data d of the cosine component of the signal extracted from the received wave is supplied from the canceller 15 to the second latch circuit 102. From the latch circuits 101 and 102, the data b and d of the sine and cosine components of the signal are supplied to the first ROM 104, and, from this ROM 104, the absolute value l(t+Δt) of the intensity of the received ultrasonic beam is supplied to the second ROM 106. Since the data b and d of the sine and cosine components of the received signal have been supplied from the first and second latch circuits 101 and 102 respectively to the second ROM 106 to be used for the computation of the value of the angle δ according to the expression (8), the computed value of the angle δ at time (t+Δt) is supplied from the second ROM 106 to the fourth ROM 108. The data output of the first ROM 104 or the absolute value $l_t$ of the intensity of the signal contracted from the preceding ultrasonic beam received at time t has been supplied to the third delay circuit 105 to be delayed by the setting of the time interval Δt of ultrasonic beam transmission. absolute value $l_t$ of the intensity of the signal extracted from the preceding ultrasonic beam received at time t is supplied from the third delay circuit 105 to the third ROM 107. Since the data a and c of the sine and cosine components of the signal extracted from the preceding ultrasonic beam received have been supplied to this ROM 107 from the first and second delay circuits 103A and 103B respectively to be used for the computation of the value of the angle θ according to the expression (7), the computed value of the angle θ at time t is supplied from the third ROM 107 to the fourth ROM 108 to be used for the computation of the displacement angle Δθ according to the expression (10). This computed value of Δθ is supplied to the fifth ROM 110 together with the value of Δt supplied from the Δt setting circuit 109 to be used for the computation of the angular velocity ω according to the expression (11), and the computed value of ω is supplied to the speed dispersion operating circuit 17 and DSC 21.

Figure 7:
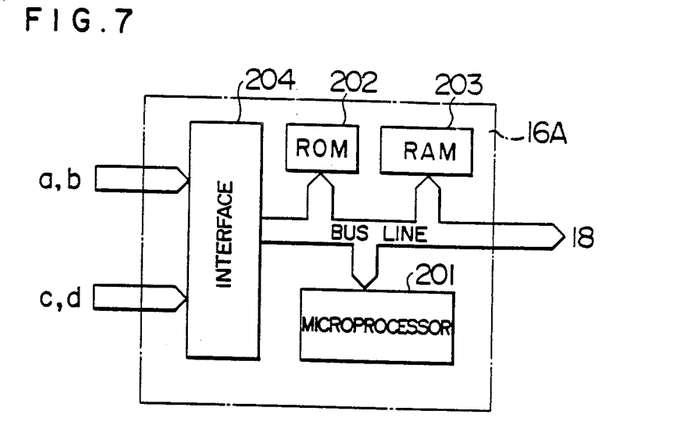
FIG. 7 is a block diagram showing the detailed structure of another form of the speed operating circuit shown in FIG. 1.

Another form of the speed operating circuit 16 is shown in FIG. 7. Referring to FIG. 7, the speed operator 16A includes a microprocessor 201, a ROM 202, a RAM (a random access memory) 203 and an interface 204 connected together by a bus line. In this speed operating circuit 16A, the expressions (1) to (11) are computed according to a programmed software.

The detailed structure of one form of the speed dispersion operating circuit 17 shown in FIG. 1 will be described with reference to FIG. 8.

The computation of the speed dispersion σ carried out in this speed dispersion operating circuit 94 is expressed as follows:

$$\sigma^2 = \frac{1}{n} \sum_{i=1}^{n} (v_1 - N)^2 \text{ or } \sigma = \sqrt{\frac{1}{n} \sum_{i=1}^{n} (v_i - N)^2} \quad (12)$$

$$N = \frac{1}{n} \sum_{i=1}^{n} v_i \quad (13)$$

where $v_i$[i : 1 to n (an integer)] is the moving speed computed by the speed operating circuit 16, and $\overline{N}$ is the average speed.

Figure 8:
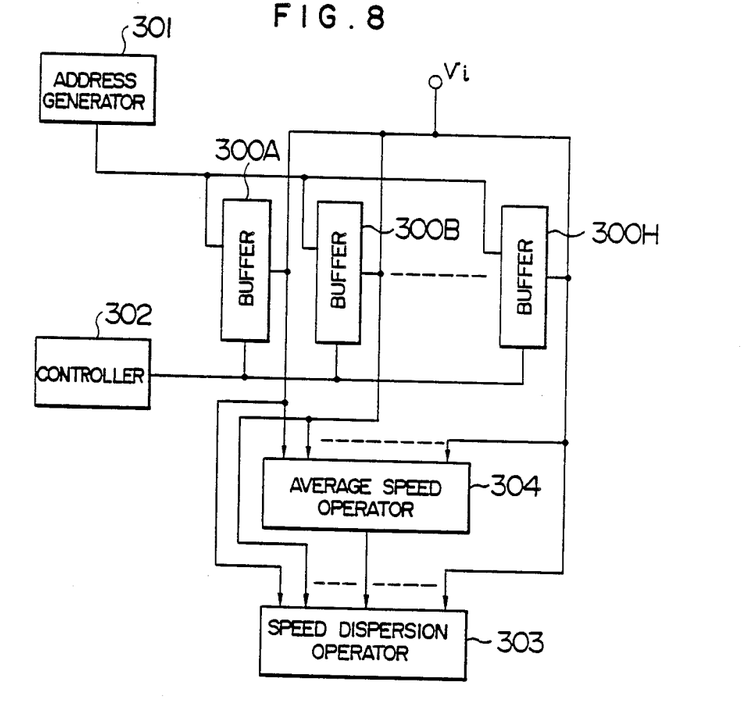
FIG. 8 is a block diagram showing the detailed structure of one form of the speed dispersion operating circuit shown in FIG. 1.

Referring to FIG. 8, buffers 300A to 300H store data of the moving speed $v_i$. These buffers 300A to 300H are, for example, such that each of them has a capacity enough to store speed data extracted from the reflected wave of one ultrasonic beam.

An address generator 301 generates addresses of the buffers 300A to 300H. These buffers 300A to 300H are selected under control of a controller 302 which is included in a control apparatus controlling the entire system. An ordinary operator 303 executes the computation of the speed dispersion σ according to the expression (12). Another ordinary operator 304 computes the average speed $\overline{N}$ according to the expression (13).

The operation of the entire ultrasonic diagnosis apparatus embodying the present invention will now be described with reference to FIG. 1.

The ultrasonic pulse beam transmitted from the ultrasonic probe 1 is generated by and applied from the transmitter circuit 2. The transmitted ultrasonic pulse beam is reflected from an internal moving medium of a living body, and the reflected ultrasonic beam is received by the ultrasonic probe 1. The received signal including the internal information of the living body is amplified by the high-frequency amplifier circuit 3. The stable high-frequency signal generated from the crystal oscillator 4 is converted by the synchronizing circuit 5 into the reference signal having the frequency corresponding to the recurrence frequency of the ultrasonic pulse beam, and the reference signal is applied to the mixer 8. The received signal amplified by the high-frequency amplifier circuit 3 is applied to the mixer 8 to be mixed with the reference signal.

Also, the reference signal is applied to the phase shifter 6 to be shifted by 90° in its phase, and the output signal of the phase shifter 6 is mixed with the signal received by the ultrasonic probe 1 and amplified by the high-frequency amplifier circuit 3, so as to provide information of the moving direction of the internal moving medium of the living body. In order to extract the Doppler components bearing the kinetic information of the internal moving medium of the living body, the output signals of the mixers 7 and 8 are applied to the cancellers 14 and 15 respectively. The individual signals including only the Doppler components extracted by the cancellers 14 and 15 are used for the computation according to the aforementioned procedure in the speed operating circuit 16 to find the value of the speed $v_i$. The speed deviation operating circuit 17 makes necessary computations according to the aforementioned procedure to find the value of the speed dispersion σ. The computed values of the speed $v_i$ and speed dispersion σ are stored in the DSC 21. Whether the computation to find the speed $v_i$ only is to be executed or the computation to find both the speed $v_i$ and the speed dispersion σ is to be executed is determined by the operation selection setting circuit 19, and the operation selector switch 18 is opened or closed.

Further, the detector 20 detects the signal indicative of the sectional image of the internal moving medium of the living body from the living-body signal received by the ultrasonic probe 1 and amplified by the high-frequency amplifier circuit 3, and the output signal of the detector 20 is also stored in the DSC 21.

The low-pass filter 10 removes the high-frequency component of the output signal of the mixer 7, and the output signal of the low-pass filter 10 is applied to the sample and hold circuit 11. In order to extract the Doppler shift component from the output signal of the low-pass filter 10, the gate pulse signal generated from the sampling pulse generator 9 is applied to the sample and hold circuit 11. As a result, the signal indicative of the Doppler shift of the internal moving medium of the living body is extracted in the sample and hold circuit 11. The output signal of the sample and hold circuit 11 is smoothed by the band-pass filter 12 and is then applied to the frequency analyzing circuit 13 which extracts the one-dimensional Doppler shift signal. This extracted Doppler shift signal is also stored in the DSC 21.

The data stored in the DSC 21 are supplied to the display unit 22 to be displayed thereon. The pattern of the picture information displayed on the display unit 22 is selected under control of the system control apparatus (not shown).

All the ROM's of the speed operating circuit 16 may have tables of the results of individual computations written therein so that the speed $v_i$ can be computed at a higher speed. Also, the speed dispersion operating circuit 17 may have a table of the results of computation of the average speed $\bar{N}$ so that the average speed used for the computation of the speed dispersion of the moving medium can be computed at a higher speed on the basis of the speed information stored in the buffers.

It can be seen from the foregoing description that the embodiment of the present invention illustrated in FIGS. 1 to 8 provides the following advantages:

(1) The speed of an internal moving medium of a living body can be computed in such a manner as to also follow up any change in the intensity of the signal reflected from the moving part, as shown by the expressions (1) to (11).

Therefore, the result of computation of the speed according to the present invention is more accurate than that computed according to the prior art method. Thus, more accurate data of the speed of the internal moving part of the living body can be obtained.

(2) The operating circuits 16 and 17 including ROM's are only required for computing the speed and speed dispersion respectively, thereby dispensing with the use of the autocorrelator essentially required in the prior art diagnosis apparatus. Therefore, the size of the diagnosis apparatus of the present invention can be reduced, and the cost can also be reduced.

(3) Since the operating circuits 16 and 17 including ROM's as described above are used for computing the speed and speed dispersion respectively, the speed and speed dispersion an be computed faster than prior art devices.

(4) By virtue of the advantages (1) to (3), the speed or both the speed and the speed dispersion of an internal moving medium of a living body scanned by an ultrasonic beam can be measured and computed for each depth at a high speed by the diagnosis apparatus of simple construction. Therefore, a greater amount of accurate information can be obtained for the diagnosis of an internal organ of a living body, so that the accuracy of diagnosis can be greatly improved.

While a preferred embodiment of the present invention has been described in detail by way of example, it is apparent that the present invention is in no way limited to such a specific embodiment, and many changes and modifications may be made therein without departing from the subject matter thereof.

It will be understood from the foregoing detailed description that, according to the present invention, the speed or both the speed and the speed dispersion of an internal moving medium of a living body scanned by an ultrasonic beam can be measured and computed for each depth at a high speed by a diagnosis apparatus of simple construction employing a speed operating circuit or the combination of a speed operating circuit and a speed dispersion operating circuit only. Therefore, a greater amount of accurate information can be obtained for the diagnosis of an internal organ of a living body, so that the accuracy of diagnosis can be greatly improved.

We claim:

1. An ultrasonic diagnosis apparatus comprising:
    an ultrasonic probe for transmitting an ultrasonic pulse beam toward a moving medium in a living body at a predetermined time interval $\Delta t$ defining a constant recurrence frequency and for receiving the reflected wave as a high frequency signal from a portion of the moving medium at any given depth in the living body;
    converting means for mixing the received high-frequency signal with a set of complex reference signals having a frequency n times (n: an integer) as high as the recurrence frequency of the transmitted ultrasonic pulse beam and having a complex relation therebetween, thereby converting the received high-frequency signal into complex signals including a sine component signal and a cosine component signal;
    operating means including a speed operating circuit for computing a moving speed of the moving medium at said given depth in the living body on the basis of said complex signals, said speed operating circuit including means for obtaining values a and b of said sine component signal at time t and time $(t+\Delta t)$, respectively, and values c and d of said cosine component signal at said times t and $(t+\Delta t)$, respectively, to compute intensities $l_t$ and $l_{(t+\Delta t)}$ of the received signal represented by equations $$l_t = (a^2 + c^2)^{\frac{1}{2}}$$

and $$l_{(t+\Delta t)} = (b^2 + d^2)^{\frac{1}{2}},$$

for using the computed values of intensities $l_t$ and $l_{(t+\Delta t)}$ to compute angular displacements $\theta$ and $\delta$, respectively, by equations $$\theta = \sin^{-1} \frac{a}{(l_t)}$$

and $$\delta = \sin^{-1} \frac{b}{(l(t+\Delta t))}$$

and for using the computed values of angular displacements $\theta$ and $\delta$ and the value of said predetermined time interval $\Delta t$ to compute a Doppler shift frequency $f_d$ represented by $$f_d = 2\pi \cdot (\delta - \theta) / \Delta t,$$

the moving speed of the moving medium at said given depth in the living body being determined from the computed Doppler shift frequency $f_d$; and
    display means for displaying in real time the moving speed computed by said speed operating circuit.

2. An ultrasonic diagnosis apparatus as claimed in claim 1, wherein said operating means includes a speed dispersion operating circuit for computing a dispersion $\sigma$ of the moving speed computed by said speed operating circuit when said moving medium is a fluid in the living body, said dispersion being defined by the equation $$\sigma = \frac{1}{n} \sqrt{\sum_{i=1}^{n} (v_i - N)^2},$$

$v_i$ being a value of the moving speed at said given depth in the living body computed by said speed operating circuit and N being an average speed defined by the equation $$N = \frac{1}{n} \sum_{i=1}^{n} v_i,$$

and operating selecting means associated with said operating means for selecting whether only the computation of the moving speed by said speed operating circuit is to be executed or both the computation of the moving speed by said speed operating circuit and the computation of the speed dispersion by said speed dispersion operating circuit are to be executed.

3. An ultrasonic diagnosis apparatus as claimed in claim 2, wherein said speed dispersion operating circuit comprises an average speed operator for receiving said values $v_i$ of the moving speed to determine said average speed $\overline{N}$, and a speed dispersion operator for receiving said values $v_i$ of the moving speed and said average speed $\overline{N}$ to compute said speed dispersion $\sigma$.

4. An ultrasonic diagnosis apparatus as claimed in claim 1, wherein said speed operating circuit comprises:

a first latch circuit for temporarily latching the values a and b of said sine component signal;

a second latch circuit for temporarily latching the values c and d of said cosine component signal;

a first operator for receiving outputs of said first and second latch circuits to compute said intensities l and $l_{(t+\Delta t)}$;

a first delay circuit connected to an output of said first latch circuit for delaying an output of said first latch circuit by $\Delta t$;

a second delay circuit connected to an output of said second latch circuit for delaying an output of said second latch circuit by $\Delta t$;

a third delay circuit connected to an output of said first operator for delaying an output of said first operator by $\Delta t$;

a second quarter for receiving outputs of said first, second and third delay circuits to compute said angular displacement $\theta$;

a third operator for receiving the outputs of said first and second latch circuits and the output of said first operator to compute said angular displacement $\delta$; and a fourth operator for receiving the outputs of said second and third operators and the value of said predetermined time interval $\Delta t$ to compute said Doppler shift frequency $f_d$.

* * * * *